United States Patent [19]

Batorewicz

[11] 4,054,543
[45] Oct. 18, 1977

[54] PHOSPHORUS-CONTAINING POLYOLS AS FLAME RETARDANT AGENTS FOR POLYURETHANES

[75] Inventor: Wadim Batorewicz, New Haven, Conn.

[73] Assignee: Uniroyal, Inc., New York, N.Y.

[21] Appl. No.: 663,173

[22] Filed: Mar. 2, 1976

Related U.S. Application Data

[62] Division of Ser. No. 543,289, Jan. 23, 1975, Pat. No. 3,970,726.

[51] Int. Cl.$^2$ .............................................. C08K 5/52
[52] U.S. Cl. ........................ 260/2.5 AJ; 260/45.8 R; 260/45.95 L; 260/77.5 AR
[58] Field of Search .................. 260/2.5 AJ, 45.8 R, 260/45.95 L, 77.5 AR

[56] References Cited

U.S. PATENT DOCUMENTS

| | | | |
|---|---|---|---|
| 3,525,711 | 8/1970 | Jenkner | 260/77.5 AR |
| 3,609,107 | 9/1971 | Boyer et al. | 260/77.5 AR |
| 3,664,975 | 5/1972 | Kerst | 260/77.5 AR |
| 3,784,592 | 1/1974 | Leonard | 260/45.95 L |
| 3,883,478 | 5/1975 | Gresham | 260/45.8 R |
| 3,945,954 | 3/1976 | Batorewicz | 260/77.5 AR |
| 3,998,764 | 12/1976 | Vollmer et al. | 260/2.5 AJ |

Primary Examiner—Donald E. Czaja
Assistant Examiner—R. A. White
Attorney, Agent, or Firm—Anthony Lagani

[57] ABSTRACT

Phosphate esters having the formula

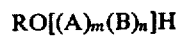

$$RO[(A)_m(B)_n]H$$

wherein A has the structural formula

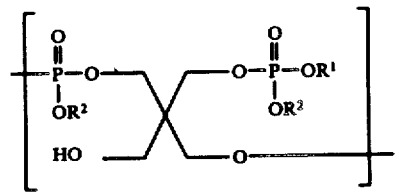

and B has the structural formula

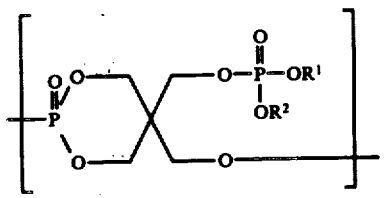

wherein the R groups are alkyl radicals, $m$ and $n$ are each integers from 0 to 4 and the sum of $m + n$ is from 1 to about 4, are useful as flame retardants, especially for rigid polyurethane foams.

6 Claims, No Drawings

PHOSPHORUS-CONTAINING POLYOLS AS FLAME RETARDANT AGENTS FOR POLYURETHANES

This is a division of application Ser. No. 543,289, filed Jan. 23, 1975, now U.S. Pat. No. 3,970,726.

BACKGROUND OF THE INVENTION

1. Field of the Invention

This invention relates to novel phosphate esters prepared from polycyclic phosphorohalidites. These esters, which are useful as flame retardants especially for rigid polyurethane foams, have the formula:

wherein A has the structural formula

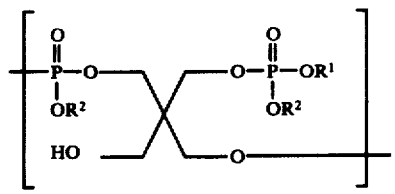

and B has the structural formula

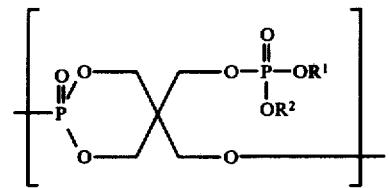

wherein R, $R^1$, and $R^2$ are the same or different and are alkyl radicals, and $m$ and $n$ are integers from 0 to about 4, the sum of $m$ plus $n$ being from one to about four. It is understood that structures A and B are randomly distributed within these oligomeric compounds.

DESCRIPTION OF THE PRIOR ART

Bliznyuk et al., Zh. Obshch. Khim, 34, p. 1169-70 (1960), teach reacting $PCl_3$ with an excess of alcohol in the presence of chlorine to produce $PO(OR)_3$. Frank et al. J. Org. Chem., 31, p. 872-875 (1966), converted simple trialkyl phosphites $(RO)_3P$ to the corresponding phosphates $(RO)_3PO$ in a similar fashion.

Neither of the above references however disclose the conversion of polycyclic phosphorohalidites to the phosphate esters of this invention.

SUMMARY OF THE INVENTION

It is an object of this invention to provide new phosphate esters. It is a further object of this invention to present a process for preparing such phosphate esters. It is another object of this invention to prepare flame resistant polymers with the use of said phosphate esters, and it is still another object of this invention to prepare flame retardant polyurethane and polyester polymers, especially rigid polyurethane foams with the inclusion therein of the co-reactive phosphate esters.

DESCRIPTION OF THE PREFERRED EMBODIMENTS

Polycyclic phosphorohalidites are used for the preparation of the phosphate esters of this invention. These phosphorohalidites precursors have the general formula $(C_5H_8O_4P_2)X_uY_n$ wherein the substituents X and Y may either be halogen or alkoxy radicals as described hereinafter.

The phosphate esters of this invention are prepared from the above phosphorohalidites resulting in the new compounds of the general formula

wherein A has the structural formula

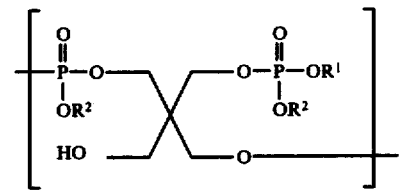

and B has the structural formula

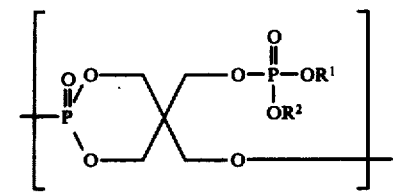

wherein R, $R^1$ and $R^2$ may be same or different and are selected from primary alkyl radicals having from 1 to about 6 carbon atoms and haloalkyl or hydroxyalkyl radicals having from 2 to 6 carbon atoms. These radicals may be either linear or branched. Examples of such radicals, but not in limitation hereof, include methyl, ethyl, propyl, n-butyl, isobutyl, n-pentyl, 2-methylbutyl, 3-methyl-butyl, neopentyl, n-hexyl, 2-methylpentyl, 3-methylpentyl, 4-methylpentyl, 2-chloroethyl, 2-bromoethyl, 2- or 3-chloropropyl, 2- or 3-bromopropyl, 2,3-dirbomopropyl, 2,3-dichloropropyl, 4-chlorobutyl, 5-chloropentyl, 6-chlorohexyl, 2-hydroxyethyl, 3-hydroxypropyl, 4-hydroxybutyl, 5-hydroxypentyl and 6-hydroxyhexyl.

The polycyclic phosphorohalidite precursors are known compounds of the general formula $(C_5H_8O_4P_2)X_uY$, wherein X is bromine or preferably chlorine, Y is an $OR^3$ group wherein $R^3$ is an alkyl or haloalkyl radical selected from the same groups as R above, but not a hydroxyalkyl radical, $u$ and $v$ each have the values of 0, 1 or 2, and the sum of $u$ plus $v$ is 2. These precursors may also be represented by the structural formulae

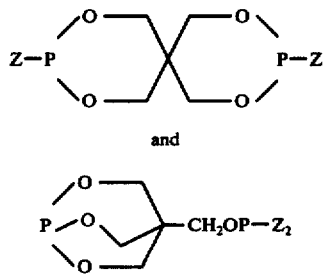

which are isomers and wherein Z has the meanings of X or Y as defined above. Although the polycyclic precursors wherein the substituent groups (X) are halogen are called phosphorohalidites, and wherein the substituent groups (Y) are $OR^3$ are usually named phosphites, the latter compounds shall be included under the general term phosphorohalidites for the purpose of this disclosure.

Polycyclic phosphorohalidites may be prepared from phosphorus trihalides such as $PCl_3$ or $PBr_3$ and and pentaerythritol according to the method described by H. J. Lucas et al. J.A.C.S. Vol. 72, p. 491–497 (1950). The conversion from halogen to $OR^3$ substitution may be made in accordance with U.S. Pat. No. 2,961,454 (Gould et al.). It has been found that the freshly prepared spirocyclic or bicyclic compounds, with time, isomerize to form an equilibrium mixture containing both structural isomers. Either isomer or a mixture thereof is suitable for the preparation of the inventive esters. In view of the phosphorohalidites being solids they are conveniently prepared in the presence of an inert solvent. Subsequent preparation of the phosphite esters of this invention may be conveniently carried out using the phosphorohalidite solution thus obtained without prior recovery of the precursor. It is advantageous to choose a solvent wherein not only the precursor but also the ester is soluble, thus chlorinated hydrocarbons such as carbon tetrachloride, chloroform, ethylene dichloride, methylene dichloride, and the like are especially suitable. The preferred solvent is ethylene dichloride. Since the spirocyclic precursor is more soluble in the above mentioned solvents, it is the preferred form for use herein.

The compounds of this invention are prepared by the addition of a polycyclic phosphorohalidite to a primary aliphatic alcohol in the presence of chlorine. Said alcohols have the general formula HOQ, wherein Q has the same meanings as $R,R^1$ and $R^2$ defined above.

The use of secondary or tertiary alcohols for the making of similar products according to the process of this invention while possible is not recommended because of the tendency of such alcohols to form hypohalides in the presence of $Cl_2$. Hypohalides may decompose rapidly, even explosively, at ambient temperatures.

When preparing the esters of this invention the ratio of alcohol must be controlled within certain limits in order to prevent undesirable side reactions. If the ratio is too low, Arbuzov type rearrangements may take place; if the ratio is too high, pentaerythritol and non-polycyclic or polymeric trialkyl phosphates are produced. Therefore, the molar ratio of HOQ to X plus Y should be equal to from $(2u + v):1$ $10(2u+v):1$ said ratio not exceeding a value of 20:1.

If $u$ equals 2 and $v$ equals 0, the preferred molar ratio of HOQ to $X+Y$ has a value of from 5 to 15 most preferably from 8 to 12. If $u$ equals 0 and $v$ is 2, the preferred molar ratio range may be from 2 to 7, the most preferred ratio being from 3 to 5. Within these limits, the ratio of the reactants may be varied as desired to produce phosphate esters having a wide range of hydroxyl numbers. For instance, if X is chlorine, the alcohol is ethanol and the ratio is 15, esters having an OH number of about 190-200 are produced, while a ratio of 8 leads to a product with an OH number of about 110-130. If X is chlorine, the alcohol is 2-chloroethanol, and the ratio is 6, the resultant product has an OH number of about 120, while at a ratio of 5 an OH number of about 90 results.

While agitating the reaction mixture, the polycyclic phosphorohalidite (diluted with an appropriate inert solvent if so desired) is added continuously or incrementably to the alcohol. The alcohol may optionally be diluted with an inert organic solvent in which the reactants and the resultant phosphate esters are soluble.

Simultaneously, but separately to the addition of the phosphorohalidite, chlorine is charged to the alcohol. The rate of addition of the two ingredients is maintained at a molar ratio of halogen to phosphorohalidite of at least 2:1. Usually a slight excess of halogen is used, preferably not exceeding 10 mole percent. A convenient way to maintain the proper concentration of chlorine during the reaction and to ensure that chlorine is in a slight excess, is by monitoring the potential of the reaction medium with a standard potentiometer fitted with a redox probe consisting of a platinum measuring probe with a standard calomel reference electrode. This operation is carried out by selecting a potential which is below that observed for the reaction medium, e.g. the solvent or alcohol or mixtures thereof saturated with chlorine. In the case of a potentiometer with a scale from zero to 1400 mv, for example, this operation is carried out at a potential below 1400 mv, usually in the range from 500 mv to 900 mv. An excess of chlorine may also be followed visually by the appearance of a greenish color in the reaction mass. The reaction is completed when, after addition of all of the polycyclic phosphorohalidite, the resulting solution maintains a permanent greenish color and no further uptake of halogen is observed.

Alternatively, when Y is $OR^3$ and $v$ is 2, the polycyclic starting material may be dissolved in the alcohol using an appropriate solvent if desired such as ethylene dichloride, and then subsequently treated with chlorine until the reaction is complete.

The process of this invention is exothermic and requires cooling to maintain a temperature of from about $-20°$ C to about $80°$ C, preferably $20°$ C to $40°$ C.

Upon the completion of the reaction, the phosphate esters may be recovered by stripping the solution under vacuum at about $30°-50°$ C to remove the bulk of the hydrogen chloride produced during the reaction. The solution is then neutralized by any conventional method, such as by the addition of sodium bicarbonate, aqueous sodium or potassium hydroxide, or an alcoholate salt. Neutralization may also be performed by using an epoxide such as ethylene or propylene oxide. Alternatively, the reaction mixture may first be neutralized and then stripped as described above.

The neutralized mixture is then subjected to vacuum distillation to remove any residual solvent or alcohol as well as any volatile by-products such as haloalkanes or chlorohydrins. The phosphate ester is then recovered as the distillation residue.

EXAMPLE I

Preparation of
3,9-Dichloro-2,4,8,10-tetraoxa-3,9-diphosphaspiro [5.5] undecane

This polycyclic phosphorochloridite precursor is prepared in the following manner: To a 2-liter, 3-necked round bottom flask equipped with a condenser, a stirrer, a thermometer, a dropping funnel and a nitrogen inlet tube, is added $PCl_3$ (280,0 g. 2.04 moles) dropwise to a stirred suspension of pentaerythritol (136.0 g, 1.0 mole) in dichloroethane (240 ml). The reaction mixture is kept at $35°-50°$ C by means of a water bath. During the addition the system is kept under a gentle nitrogen sweep to facilitate the removal of the HCl formed. When the $PCl_3$ addition is completed, the temperature of the reaction mixture is slowly raised to reflux over about a one hour period. The mixture is then kept under reflux, using a vigorous nitrogen sweep, until a homogeneous solution is obtained, i.e. about one to two hours. Trace amounts of white precipitate may separate from the reaction solution upon cooling to room temperature. This small amount of precipitate, consisting mostly of pentaerythritol, is removed by filtration. The filrate contains the desired product, 3,9-dichloro-2,4,8,10-tetraoxa-3,9-diphosphaspiro[5,5] undecane, and is essentially free of by-products. The phosphorochloridite precursor thus obtained is used in the subsequent reactions without further purification.

EXAMPLE II

Methyl Phosphate Ester

This example represents the general procedure for the preparation of the compounds of this invention by oxidation of a phosphorochloridite with chlorine in presence of an alcohol.

Methanol (240 g, 7.5 moles) is stirred and cooled to 5° to 10° C by means of an acetone-ice bath in a reaction vessel fitted with a thermometer, an addition funnel, and a gas inlet tube connected to a chlorine gas cylinder. Chlorine (2 moles) and the phosphorochloridite (1 mole) of Example I are added simultaneously to the methanol maintaining a slight chlorine excess, as evidenced by the greenish color of the reaction medium. During the addition, the reaction mixture is maintained at about 25° to 35° C by means of the acetone-ice bath as well as by controlling the rates of addition of the reactants. When the addition of phosphorochloridite is completed, the resulting greenish solution is distilled under 10–20 mm $H_g$ pressure at about 30°–50° C in order to remove most of the HCl formed during the reaction. The residual acidic solution is then treated with propylene oxide at 40°–60° C until neutral to moist litmus paper. Low boiling materials are then further removed from the reaction solution by distillation under 10–20 mm. $H_g$ and subsequently 0.5 mm. $H_g$ at about 100° C. The residue is the methyl phosphate ester, a clear fluid oily material.

Analysis: 12.5% P: 0.8% Cl; OH#203

In Examples III to X inclusive, the spirocyclic compound described in and prepared essentially according to Example I is used exclusively.

EXAMPLE III

Methyl Phosphate Exter

The procedure of Example II is repeated except that 15 moles of methanol are placed in the reaction vessel, the overall methanol to phosphorochloridite mole ratio being 15.

Analysis: 16.4% P: 0.5% Cl: OH #287

EXAMPLE IV

Ethyl Phosphate Ester

The procedure of Example II is repeated except that 15 moles of ethanol are used in place of the methanol. The mole ratio of ethanol to phosphorochloridite being 15. The resultant product is a clear fluid oil.

Analysis: 14.7% P: 0.4% Cl: OH #190

EXAMPLE V

Ethyl Phosphate Ester

The procedure of Example IV is repeated except that 8 moles of ethanol are used. The overall molar ratio of alcohol to phosphorochloridite being 8. The product is a clear fluid oil.

Analysis: 14.6% P: 0.7% Cl: OH #130

EXAMPLE VI n-Butyl Phosphate Ester

The procedure of Example II is repeated except that methanol is replaced by n-butanol, and the molar ratio of n-butanol to the phosphorochloridite employed is 7.0. The product is a white waxy solid.

Analysis: 13.6% P: OH#105

EXAMPLE VII

2-Chloroethyl Phosphate Ester

The procedure of Example II is repeated except that methanol is replaced by 2-chloroethanol, and the ratio of 2-chloroethanol to the phosphorochloridite employed is 4.5. The product obtained is a clear oil.

Analysis: 13.8% P: 19.8% Cl: OH #91

EXAMPLE VIII

2,3-Dibromopropyl Phosphate Ester

The procedure of Example II is repeated except that methanol is replaced by 2,3-dibromopropanol at a molar ratio of 2,3-dibromopropanol to the phosphorochloridite of 6. The resultant product is a dark tan viscous oil.

Analysis: 7.0% P: 56.2% Br: 1.7% Cl: OH #76

EXAMPLE IX

2-Hydroxyethyl Phosphate Ester

The procedure of Example II is repeated except that methanol is replaced by ethylene glycol at a molar ratio of ethylene glycol to the phosphorochloridite of 6. The product is a clear oil.

Analysis: 11.9% P: OH #432

EXAMPLE X

3-Hydroxypropyl Phosphate Ester

The procedure of Example II is repeated except 1,3-propanediol is used instead of methanol. A 4 to 1 molar ratio of the alcohol to phosphorochloridite is maintained. The product is an oil.

Analysis: 10.4% P: OH #363

Example XI

2-Chloroethyl Phosphate Ester

This example represents an alternate procedure for the preparation of the phosphate esters of this invention by chlorination of a spirocyclic phosphite wherein Y is a 2-chloroethoxy group and v is 2 in the presence of an alcohol. The common intermediate, the phosphorochloridite, is prepared as described in Example I, using $PCl_3$ (280 g. 2.04 mole) and pentaerythritol (136 1.0 mole) in dichloroethane (240 ml.) as the solvent. The resulting solution is treated with ethylene oxide over a period of about 2½ hours at about 50° C in presence of $TiCl_4$ (5 drops) until neutral to moist litmus paper. The resulting solution, now containing the phosphite, 3,9-bis(2-chloroethoxy)-2,4,8,10-tetraoxa-3,9-diphosphaspiro [5.5] undecane, is diluted with 2-chloroethanol (161 g, 2 moles) and treated with chlorine gas until the solution maintains a slightly green color, indicating that substantially all of the phosphite has reacted. During oxidation, cooling with an acetone ice bath is required to keep the temperature at about 25° C. The reaction solution is neutralized with propylene oxide and concentrated first under 10–20mm $H_g$ pressure and then under 0.3mm $H_g$ pressure at about 100° C pot temperature. The product is a clear oil.

Analysis: 14.9% P: 20.1% Cl: OH #70

EXAMPLE XII

Preparation of Dichloro (2,6,7-trioxa-1-phosphabicyclo [2.2.2]oct-4-yl)methyl phosphite.

This bicyclic precursor is prepared as follows: a solution of phosphorus trichloride (91.0g., 0.66 mole) and 4-hydroxymethyl-2,6,7-trioxa-phosphabicyclo[2.2.2] octane [36.0g., 0.20 mole: prepared according to the procedure described by W. S. Wadsworth et al., J.A.C.S., 84, p. 615 (1962) in chloroform (200 ml) is stirred at room temperature for about 3 hours and then kept at refluxing temperature for one hour. The product separates from solution as white crystals. It is separated by filtration, washed with an excess of carbon tetrachloride and dried in air. The product has a melting range of 118°–120° C.

Analysis: 23.7%P: theory 23.4%P

EXAMPLE XIII

Ethyl Phosphate Ester

This example illustrates the preparation of the phosphate ester of this invention from the bicyclic phosphorohalidite of Example XII using the procedure as described in Example II except that methanol is replaced by ethanol. The mole ratio of ethanol (62.5g) to the bicyclic phosphorochloridite (30g. 0.113 moles in 75 nil of chloroform) is 12. A clear fluid oil is obtained.

Analysis: 16.0% P: OH #77

The phosphate esters of this invention are useful as flame retardants for organic polymers, particularly resins, and are effective as reactive flame retardants for polyesters and expecially for rigid polyurethane foams. The OH functionality of these phosphates allows them to be incorporated into the polymer backbone, thus providing a permanent flame retardant protection to the polymer. In addition, the preferred compositions, wherein at least $R^1$ and $R^2$ are ethyl or 2-chloroethyl, are fluid oils at room temperature and are soluble in the polyether polyols normally normally employed in polyurethane production. This is especially advantageous in polyurethane foam manufacture where homogeneity and low viscosity of the components, i.e. polyisocyanates and polyols, are essential.

When used as flame retardants in polymers such as polyesters and polyurethanes, these phosphate esters may be incorporated at concentrations of from about 2 to 40 percent, usually from 5 to 15 percent based on the total weight of the polymer.

EXAMPLE XIV

Rigid Polyurethane Foam

This example illustrates the utility as well as the superior efficacy of the compounds of the invention in rigid polyurethane foam.

The foams are prepared using a conventional oneshot process employing the recipes listed on Table I (Formulation). For this purposes, all the ingredients except the polyisocyanate are thoroughly mixed in a beaker and thereafter the polyisocyanate is added while rapidly agitating the mixture with an air-driven stirrer. The liquid contents of the beaker are then poured into a mold where within a short period of time a foam develops. The foam is cured overnight at room temperature, and the flame resistance is determined by the Oxygen Index test (A.S.T.M. D-2863).

Experiment A does not include a flame retardant, and Experiment E contains a well known flame retardant used commercially in rigid polyurethane foams. Experiments A and E are outside the scope of this invention.

In Table I the flame resistance data of the foams are summarized.

The results indicate that in all examples where the compounds of the invention are employed as the flame retardant, the oxygen indices achieved are higher than those of the blank (A) and of the comparison experiment (E). The extraordinary and unexpected improvement amounts to over 30% (Expd. C+D) when compared to the prior art compound at substantially the same concentration. Even when only one-half of the compound of the invention is incorporated in the polyurethane an improvement is achieved (B) over the comparison foam (E).

Table I

| Corporations and Results of Example XIV | | | | | |
|---|---|---|---|---|---|
| Experiment | A | B | C | D | E |
| Formulation parts by weight | | | | | |
| Polyol[1] | 100 | 87.6 | 75 | 74.2 | 74.6 |
| Surfactant[2] | 2 | 2 | 2 | 2 | 2 |
| Triethylenediamine[3] | 1 | — | — | 1 | — |
| Dimethylethanolamine[3] | — | 2 | 2 | — | 2 |
| Trichlorofluoromethane[4] | 30 | 30 | 30 | 45 | 30 |
| methylenebis(phenyl isocyanate) (crude) [5] | 136 | 121 | 127 | 115 | 126.5 |
| Phosphate of Example V | — | 12.4 | 25 | — | — |
| Phosphate of Example VII | — | — | — | 25.8 | — |
| Commercial Flame Retardant[6] | — | — | — | — | 25.4 |
| Results | | | | | |
| Oxygen Index | 20.6 | 23.6 | 24.5 | 24.9 | 23.5 |
| % Improvement[8] | — | 3.4 | 34. | 48. | — |

Remarks
(1) Propylene oxide adduct of N-aminoethylpiperazine molecular weight ca. 350. OH # ca. 530.
(2) Silicone compound, DC-193 of Dow Corning Corp.
(3) Catalyst
(4) Blowing Agent
(5) Product of Rubicon Chemicals, Inc.
(6) O-O-diethyl N,N-bis(Hydroxyethyl)aminomethylphosphonate.
(7) ASTM D-2863
(8) Calculated according to equation
% Improvement = $[OI_I - OI_E/(OI_E - OI_O)] \times 0\ 100$
wherein
$OI_I$ = Oxygen index of composition of invention
$OI_E$ = Oxygen index of Example E (comparison)
$OI_O$ = Oxygen index of composition without flame retardant (A)

EXAMPLE XV

This example illustrates that the compositions of this invention provide rigid urethane foams having excellent physical properties. The foam formulation is given in Table II. For comparison, a widely used reactive flame retardant (O,O-diethyl N,N-bis(hydroxyethyl)aminomethylphosphonate), Experiment C, is also included. The physical properties of the foams are summarized in Table II. The test data demonstrate the superior compressive strength of Experiment B of the invention over the polymer without a flame retardant (A) and the one containing a known flame retardant (C).

In addition, friability and dimensional stability after aging of sample B is superior to that of sample C which contains the commercial reactive flame retardant.

Table II

Results of Example XV

| Foam Formulation Components | A | B | C |
| --- | --- | --- | --- |
| Polyether polyol[1] | 100 | 100 | 100 |
| Silicon Surfactant (DC 193 Dow Corning) | 1.5 | 1.5 | 1.5 |
| Triethylenediamine | 1.0 | 1.0 | 1.0 |
| Dibutyltin dilaurante | 0.2 | 0.2 | 0.2 |
| Trichlorofluoromethane | 40 | 40 | 40 |
| Phosphate prepared according to Example V | — | 20.5[2] | — |
| O,O-Diethyl N,N-bis(hydroxyethyl)aminomethylphosphonate | — | — | 25.5[2] |
| Methylenebis(phenylnocyanate (crude) | | | |
| Physical Properties | | | |
| Density, psf | 1.96 | 2.19 | 2.50 |
| Compressive strength, psi: | | | |
|   Parallel to foam rise | 34.9 | 43.9 | 36.1 |
|   Perpendicular to foam rise | 19.6 | 23.7 | 19.9 |
| Friability, % loss | 13.6 | 17.7 | 23.9 |
| % Closed cells | 84.5 | 86.0 | 84.4 |
| Dimensional Stability (1 week), % Vol change | | | |
|   158° F, Dry | 1.2 | 0.4 | 0.5 |
|   158° F, 97% R | 4.3 | 6.0 | 12.0 |
|   250° F, Dry | 9.7 | 13.4 | 19.4 |

[1]Propoxylated sorbitol having an OH# of about 550.
[2]Foams were formulated to give same phosphorus concentration (ca. 0.9%) for both samples.

What is claimed is:

1. A flame retardant composition comprising a polyurethane polymer and a flame retarding effective amount of a phosphate ester of the formula

integrally part of the polymer wherein A has the structure

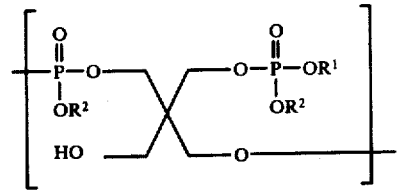

and B has the structure

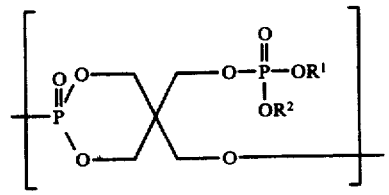

wherein R, R[1] and R[2] are the same or different and are linear or branched primary radicals selected from alkyl having 1 to 6 carbon atoms, and chloroalkyl, bromoalkyl and hydroxy alkyl having 2 to 6 carbon atoms; $m$ and $n$ are integers from 1 to about 3 and the sum of $m$ plus $n$ is from 2 to about 4.

2. The flame retardant composition of claim 1 wherein R[1] and R[2] are the same.

3. The flame retardant composition of claim 1 wherein R, R[1] and R[2] are each selected from the group consisting of methyl, ethyl, propyl, n-butyl, 2-chloroethyl, 2,3-dibromopropyl, 2-hydroxyethyl and 3-hydroxypropyl.

4. The flame retardant composition of claim 1 wherein said polyurethane polymer is a rigid polyurethane foam.

5. The flame retardant composition of claim 1, wherein said phosphate ester is present at a concentration of from 2 to 40 percent by weight based on the total weight of the polymer.

6. The flame retardant composition of claim 5 wherein said concentration is from 5 to 15 percent by weight.